(12) United States Patent
Clemente et al.

(10) Patent No.: US 9,934,589 B2
(45) Date of Patent: Apr. 3, 2018

(54) SYSTEM AND METHOD FOR DETERMINING BILIRUBIN LEVELS IN NEWBORN BABIES

(71) Applicants: Matthew James Clemente, King of Prussia, PA (US); George Stavis, Dobbs Ferry, NY (US); Noureddine Melikechi, Dover, DE (US); Robert Stavis, Bryn Mawr, PA (US)

(72) Inventors: Matthew James Clemente, King of Prussia, PA (US); George Stavis, Dobbs Ferry, NY (US); Noureddine Melikechi, Dover, DE (US); Robert Stavis, Bryn Mawr, PA (US)

(73) Assignee: Bilibaby, LLC, King of Prussia, PA (US)

( * ) Notice: Subject to any disclaimer, the term of this patent is extended or adjusted under 35 U.S.C. 154(b) by 330 days.

(21) Appl. No.: 14/677,701

(22) Filed: Apr. 2, 2015

(65) Prior Publication Data

US 2016/0012610 A1  Jan. 14, 2016

Related U.S. Application Data

(60) Provisional application No. 61/973,885, filed on Apr. 2, 2014.

(51) Int. Cl.
*A61B 5/00* (2006.01)
*G06T 7/40* (2017.01)
(Continued)

(52) U.S. Cl.
CPC ............ *G06T 7/408* (2013.01); *A61B 5/0077* (2013.01); *A61B 5/1455* (2013.01);
(Continued)

(58) Field of Classification Search
CPC . A61B 5/0077; A61B 5/14546; A61B 5/1455; A61B 5/443
See application file for complete search history.

(56) References Cited

U.S. PATENT DOCUMENTS 2,437,916 A    3/1948  Greenwald
5,259,382 A   11/1993  Kronberg
(Continued)

FOREIGN PATENT DOCUMENTS

CN        103340604 A    10/2013
WO     2013096766 A2     6/2013
(Continued)

OTHER PUBLICATIONS

Extended European Search Report in EP15772590.4 (dated Aug. 3, 2017).
(Continued)

*Primary Examiner* — Christian Jang
(74) *Attorney, Agent, or Firm* — Pryor Cashman LLP

(57) ABSTRACT

The present invention provides a system and method for determining bilirubin levels in an individual based on skin coloration using a smartphone or other personal device and an attached ancillary apparatus. The device, such as a smartphone or tablet, is capable of storing and running software. The device is also coupled to both a camera and light source to obtain data regarding the skin's coloration. Software is installed on the device to control the light source and calculate bilirubin levels in the individual based on the input received from the camera. The ancillary apparatus is a mechanism surrounding the light source and camera that is placed on the skin of the individual when the system is in use. The ancillary apparatus thus creates a light tight seal between the skin, light source and camera, enabling the system to receive the most accurate data from the camera.

44 Claims, 8 Drawing Sheets

(51) Int. Cl.
*A61B 5/145* (2006.01)
*A61B 5/1455* (2006.01)
*H04N 5/225* (2006.01)
*G06T 7/90* (2017.01)

(52) U.S. Cl.
CPC .......... *A61B 5/14546* (2013.01); *A61B 5/443* (2013.01); *A61B 5/6897* (2013.01); *A61B 5/6898* (2013.01); *A61B 5/7235* (2013.01); *G06T 7/90* (2017.01); *H04N 5/2256* (2013.01); *A61B 2503/045* (2013.01); *A61B 2560/0443* (2013.01); *G06T 2207/30088* (2013.01)

(56) References Cited

U.S. PATENT DOCUMENTS

| | | |
|---|---|---|
| 2002/0095077 A1 | 7/2002 | Swedlow et al. |
| 2012/0203086 A1* | 8/2012 | Rorabaugh .......... A61B 3/1173 600/321 |
| 2013/0023742 A1 | 1/2013 | Molcho et al. |
| 2013/0057865 A1 | 3/2013 | Meijer et al. |
| 2013/0273524 A1 | 10/2013 | Ehrenkranz |
| 2013/0296673 A1 | 10/2013 | Thaveeprungsriporn et al. |
| 2014/0018647 A1 | 1/2014 | Segman |
| 2014/0316226 A1 | 10/2014 | Ferber et al. |
| 2014/0323832 A1 | 10/2014 | Thangaraj et al. |

FOREIGN PATENT DOCUMENTS

| | | |
|---|---|---|
| WO | 2015/024151 | 7/2015 |
| WO | 2016047754 A1 | 3/2016 |

OTHER PUBLICATIONS

Jaundice Meter (JM-103) User Manual, Konica Minolta and Hill-Rom Air-Shields (Oct. 2003).

* cited by examiner

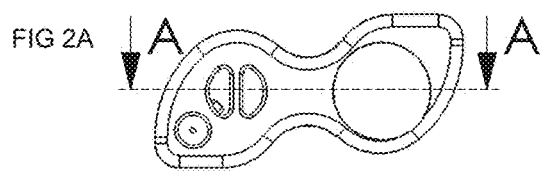
FIG 2A
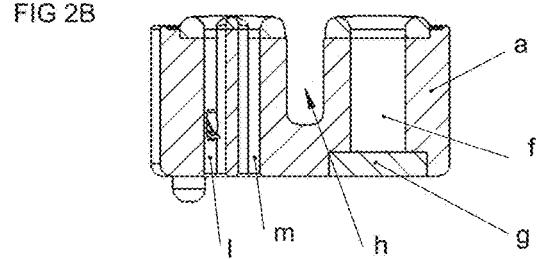
SECTION A-A
FIG 2B
FIG 2C
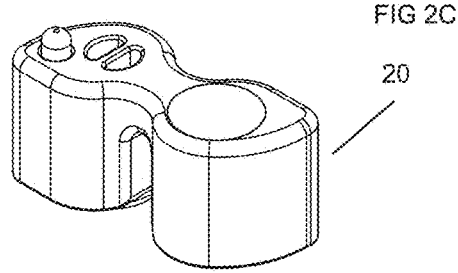
20
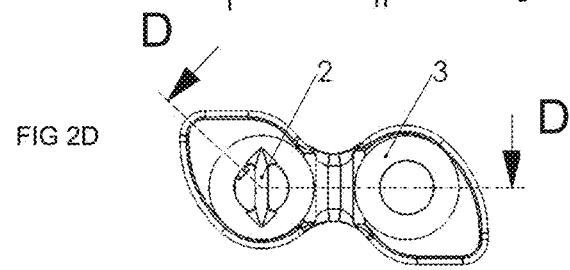
FIG 2D
FIG 2E    SECTION D-D
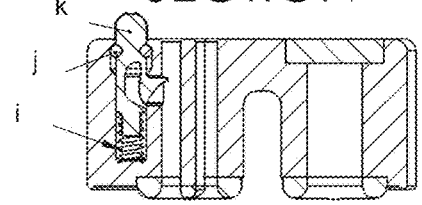
FIG 2F
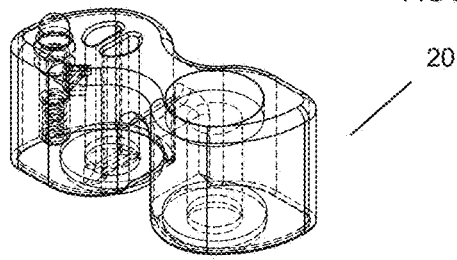
20

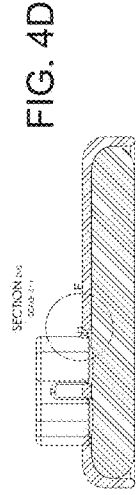
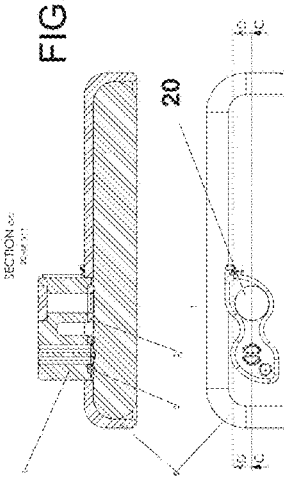
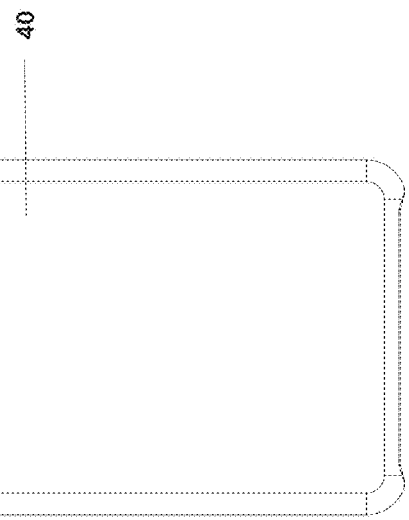
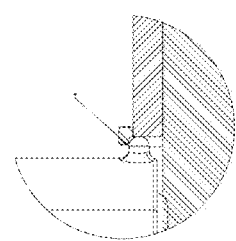
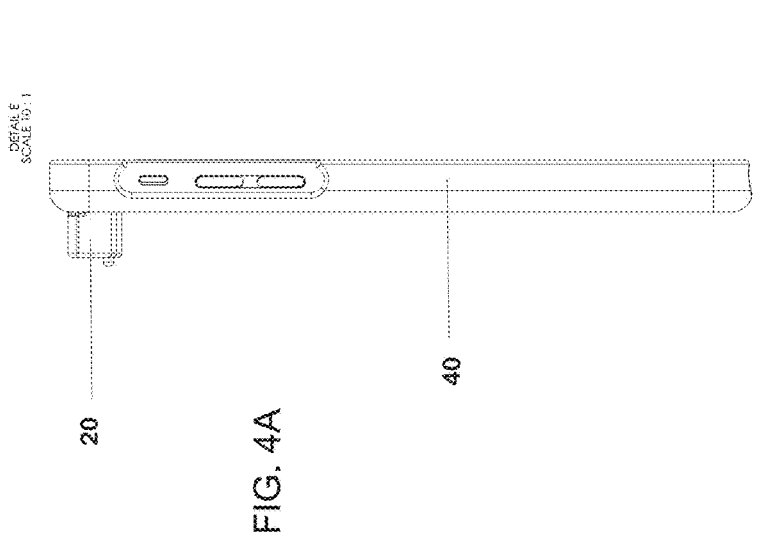
FIG. 4D
FIG. 4C
FIG. 4B
FIG. 4E
FIG. 4A

SYSTEM AND METHOD FOR DETERMINING BILIRUBIN LEVELS IN NEWBORN BABIES

RELATED APPLICATIONS

This application claims priority to U.S. Provisional Patent Application No. 61/973,885, filed Apr. 2, 2014, the disclosure and teachings of which are incorporated herein by reference.

FIELD OF THE INVENTION

The present invention relates generally to a system and method for determining levels of a substance in a patient's body based on the patient's skin coloration. The invention provides a device such as a smartphone coupled to a light source and optical detector that receives data regarding the skin coloration and uses that data to calculate the concentration of the substance in the body.

BACKGROUND OF THE INVENTION

During the first week of life, most newborns develop a visible yellow coloring of the skin—jaundice—due to an increase in a chemical called bilirubin. Moderate levels of bilirubin are benign, but very high levels—called severe hyperbilirubinemia—can cause a condition called kernicterus, which is a severe and life-long severe form of athetoid cerebral palsy with hearing dysfunction, dental-enamel dysplasia, and intellectual handicaps.

In order to reduce the likelihood of kernicterus, the American Academy of Pediatrics recommends that all infants be evaluated for jaundice with systematic measurement of bilirubin, and treated according to specific algorithms. Measurement of bilirubin levels is most accurately done by chemical analysis of a blood specimen, but handheld instruments have also been developed to estimate bilirubin levels by optical measurement of subcutaneous skin coloration. Because of prohibitively high cost, such instruments are only practical in a hospital setting, rather than in a doctor's office or for home application. There are no currently available technologies for estimating the bilirubin level at a price level consistent with use in a doctor's office or in the home. Accordingly, it is often necessary for infants to return to the hospital to have the bilirubin level checked.

The present invention described herein builds upon the functions of smartphones, tablets, computers, digital cameras connected to computers and other home devices to give parents and clinicians a noninvasive, rapid, and relatively easy to implement tool to monitor bilirubin through changes in the skin color of the infant. The invention further provides an affordable method of estimating bilirubin levels in the home or doctor's office that will simplify and vastly improve the outpatient management of hyperbilirubinemia in babies during the first week at home.

DESCRIPTION OF PRIOR ART

To the Applicant's knowledge, no prior art exists that provides a system or method for determining the levels of a substance in a patient's body based on subcutaneous skin coloration using a smartphone, tablet, personal computer, digital camera, or other personal device.

SUMMARY OF THE INVENTION

The present invention provides a system and method for determining bilirubin levels in an individual based on subcutaneous skin coloration using a smartphone or other personal device and an attached ancillary apparatus. The device, such as a smartphone or tablet, is capable of storing and running software. The device is also coupled to both a camera and light source to obtain data regarding the skin's subcutaneous coloration. Software is installed on the device to control the light source and calculate bilirubin levels in the individual based on the input received from the camera.

BRIEF DESCRIPTION OF THE DRAWINGS

FIG. 2A provides a top perspective view of the ancillary device in a smartphone embodiment having one or more physical filters or light-transmitting pathways as well as safety features and utilizing the smartphone's on-board flash and the on-board camera to capture an image and an ancillary module that has incorporated that prevent misuse;

FIG. 2B provides a cross sectional view along section A-A of the ancillary device provided in FIG. 2A;

FIG. 2C provides a angled elevational view of the ancillary device provided in FIG. 2A;

FIG. 2D provides a top perspective view of the ancillary device in an alternative smartphone embodiment having one or more physical filters or light-transmitting pathways as well as safety features and utilizing the smartphone's on-board flash and the on-board camera to capture an image and an ancillary module that has incorporated that prevent misuse;

FIG. 2E provides a cross sectional view along section D-D of the ancillary device provided in FIG. 2D;

FIG. 2F provides a angled elevational view of the ancillary device provided in FIG. 2D;

FIG. 4A depicts a side view of an embodiment of the ancillary module disclosed in FIG. 2 attached to the smartphone;

FIG. 4B depicts a rear view of a smartphone attached to an embodiment of the ancillary module disclosed in FIGS. 2A-2E;

FIG. 4C depicts a detailed cross sectional view of section C-C of the embodiment of the ancillary module disclosed in FIG. 4B;

FIG. 4D depicts a detailed cross sectional view of section D-D of the embodiment of the ancillary module disclosed in FIG. 4B;

FIG. 4E depicts a detailed view of section E shown in FIG. 4D;

DETAILED DESCRIPTION

A detailed description will now be given of the invention with reference to the attached FIGS. 1-5. It should be understood that these Figures are exemplary in nature and in no way serve to limit the scope of the invention.

Figure 1:
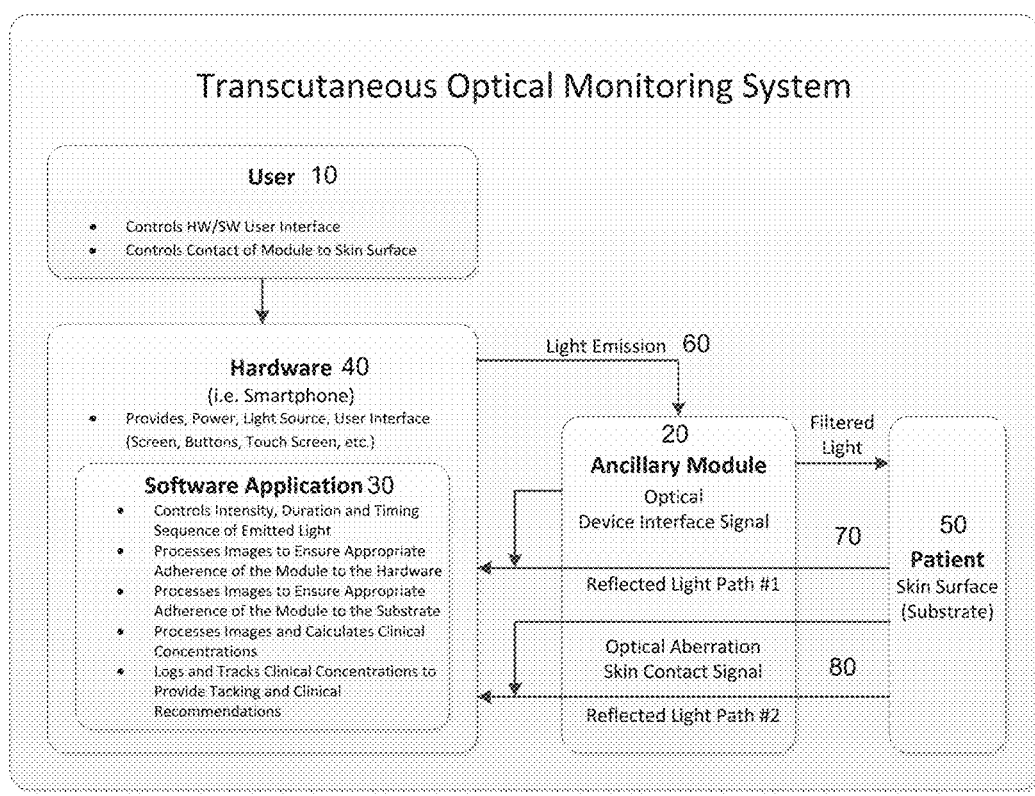
FIG. 1 is a diagram depicting the system architecture of the preferred embodiment.

The present invention describes a system and method for measuring the level of bilirubin in a patient based on subcutaneous skin coloration by using a known light source to generate reflected light that is then recorded and analyzed. This system and method utilizes optical imaging methods for obtaining tissue properties based on the emissions of known light sources 60, such as those demonstrated in FIGS. 3A-3C, and the sensing of light refraction 70 and 80 caused by tissue interactions. The difference in the optical densities found in the various pathways allows the effect of the dermal layers to be removed through analysis to obtain values for the transcutaneous bilirubin in the subcutaneous layer. At the highest level the invention consists of a user 10, a patient 50, hardware 40, such as a smartphone, a software application 30, and an ancillary module 20 as shown in FIG. 1. To use the system, a user connects the ancillary module 20 to the hardware 40, and places the ancillary module onto the patient's skin. In some applications, the user and patient are the same person. The user then, using the software 30 on the hardware 40, emits light 60 from a light source through the ancillary module onto the patient's skin. The emitted light 60 strikes the cutaneous membranes of the user 50. A fraction of the incident energy is reflected at the tissue boundary, and a fraction is transmitted inside the tissue. A portion of the transmitted light is further absorbed and scattered by the tissue. The light distribution in the tissue is affected by the refractive index and absorption scattering characteristics of the tissue. The scattered light is then transmitted through single or multiple optical pathways and detected by a sensor. The optical sensor transmits this data to the software on the device and the software uses this data to calculate the level of bilirubin or other substance in the patient.

The detailed description elaborates the methods by which the ancillary module 20 and the accompanying software application 30 will interface between the hardware 40 and the patient 50. The safety features and methods by which the module and software protects the patient, by reducing the possibility of user error, are also described.

Figure 3A:
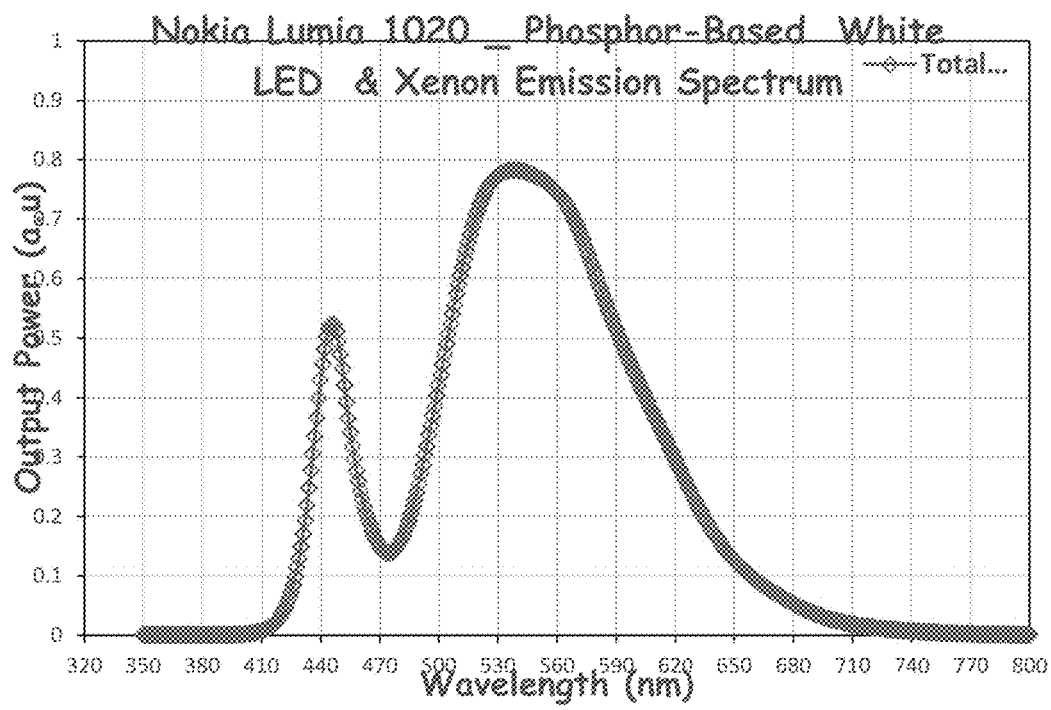
FIG. 3A provides a graph disclosing the distribution of the light source on the Nokia Lumia 1020 smartphone showing the emission of light at both the 450 nm and 550 nm wavelengths for use with the present invention.
Figure 3B:
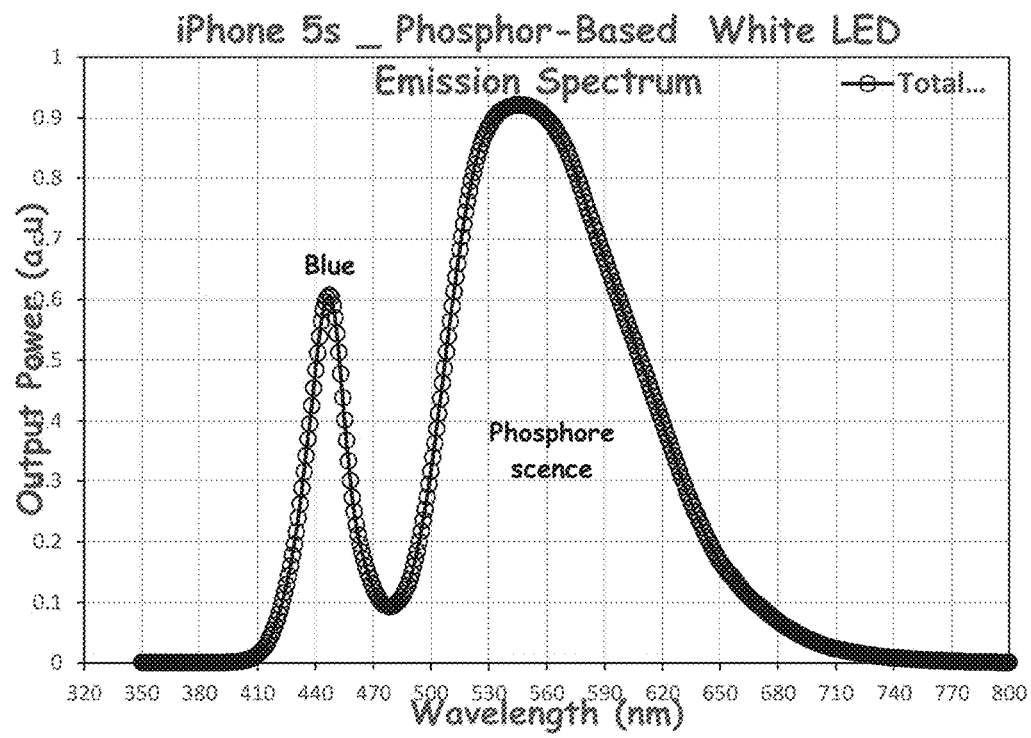
FIG. 3B provides a graph disclosing the distribution of the light source on the iPhone 5s smartphone showing the emission of light at both the 450 nm and 550 nm wavelengths for use with the present invention.
Figure 3C:
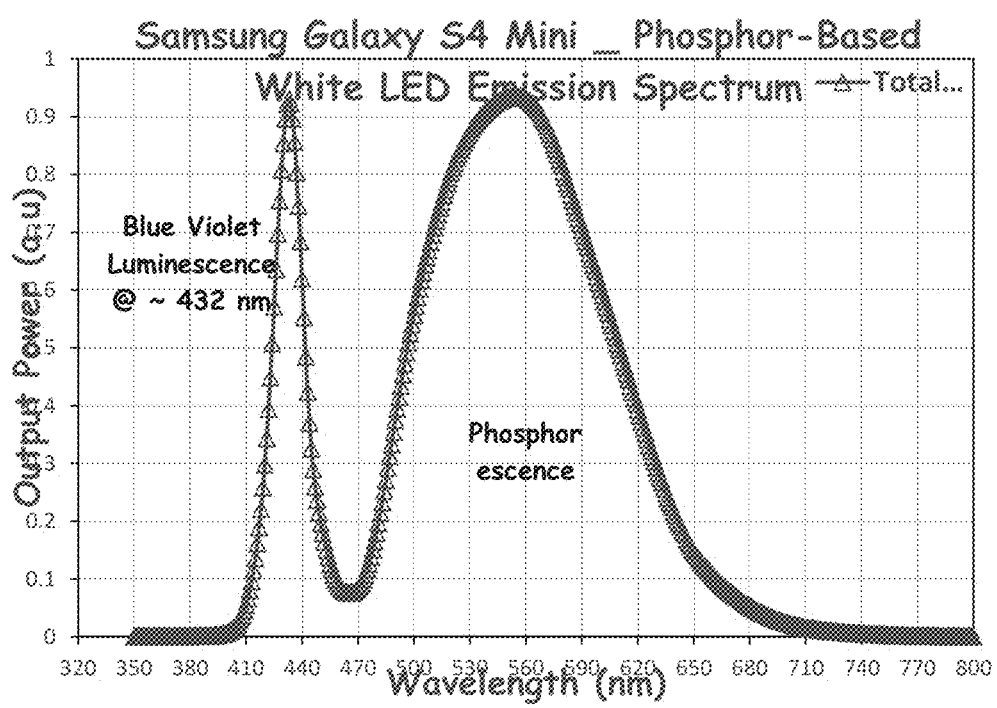
FIG. 3C provides a graph disclosing the distribution of the light source on the Samsung Galaxy S4 Mini smartphones showing the emission of light at both the 450 nm and 550 nm wavelengths for use with the present invention.
Figure 5A:
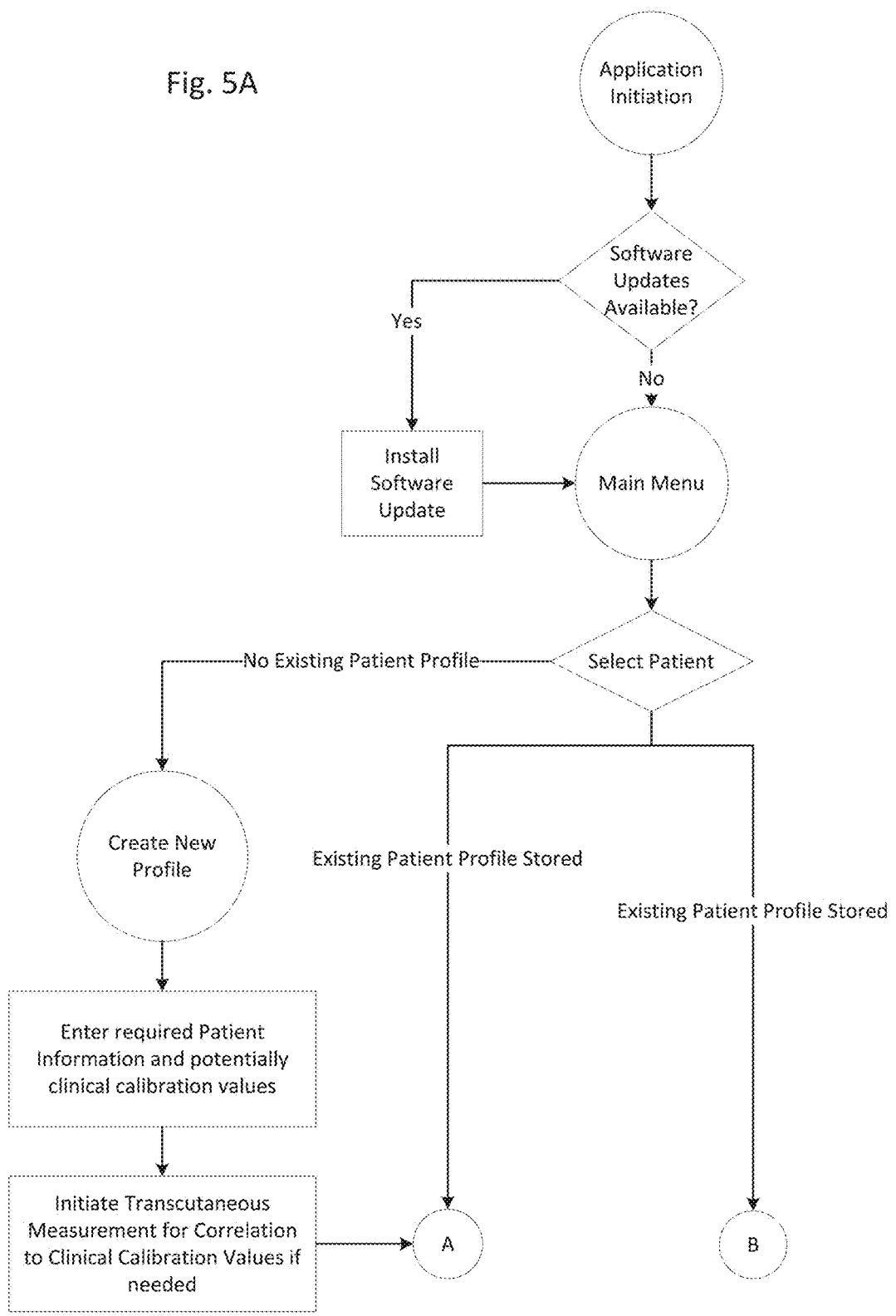
FIG. 5A is a portion of a flowchart illustrating the functions of the software of the preferred embodiment.
Figure 5B:
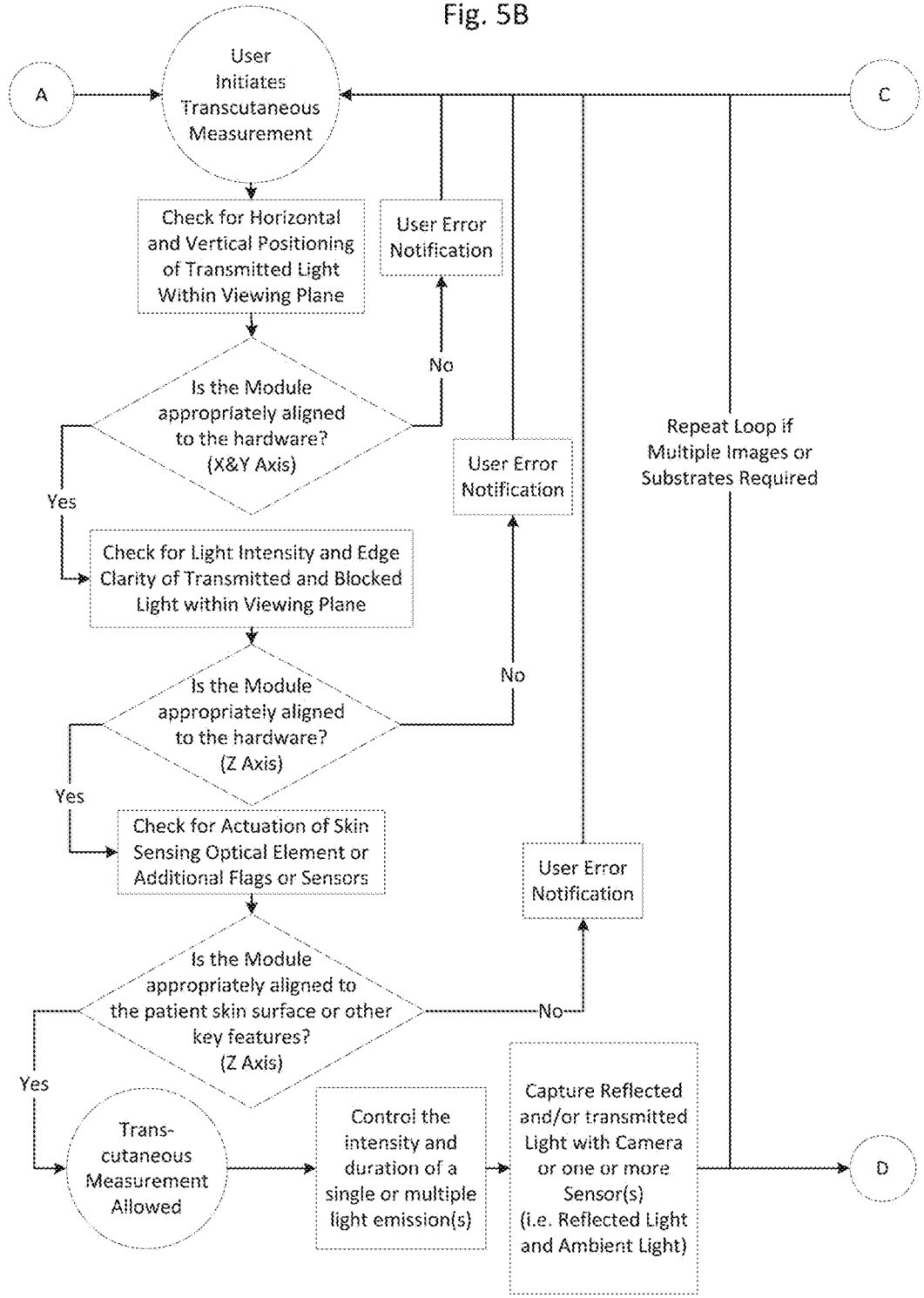
FIG. 5B is a portion of a flowchart continuing from FIG. 5A illustrating the functions of the software of the preferred embodiment.
Figure 5C:
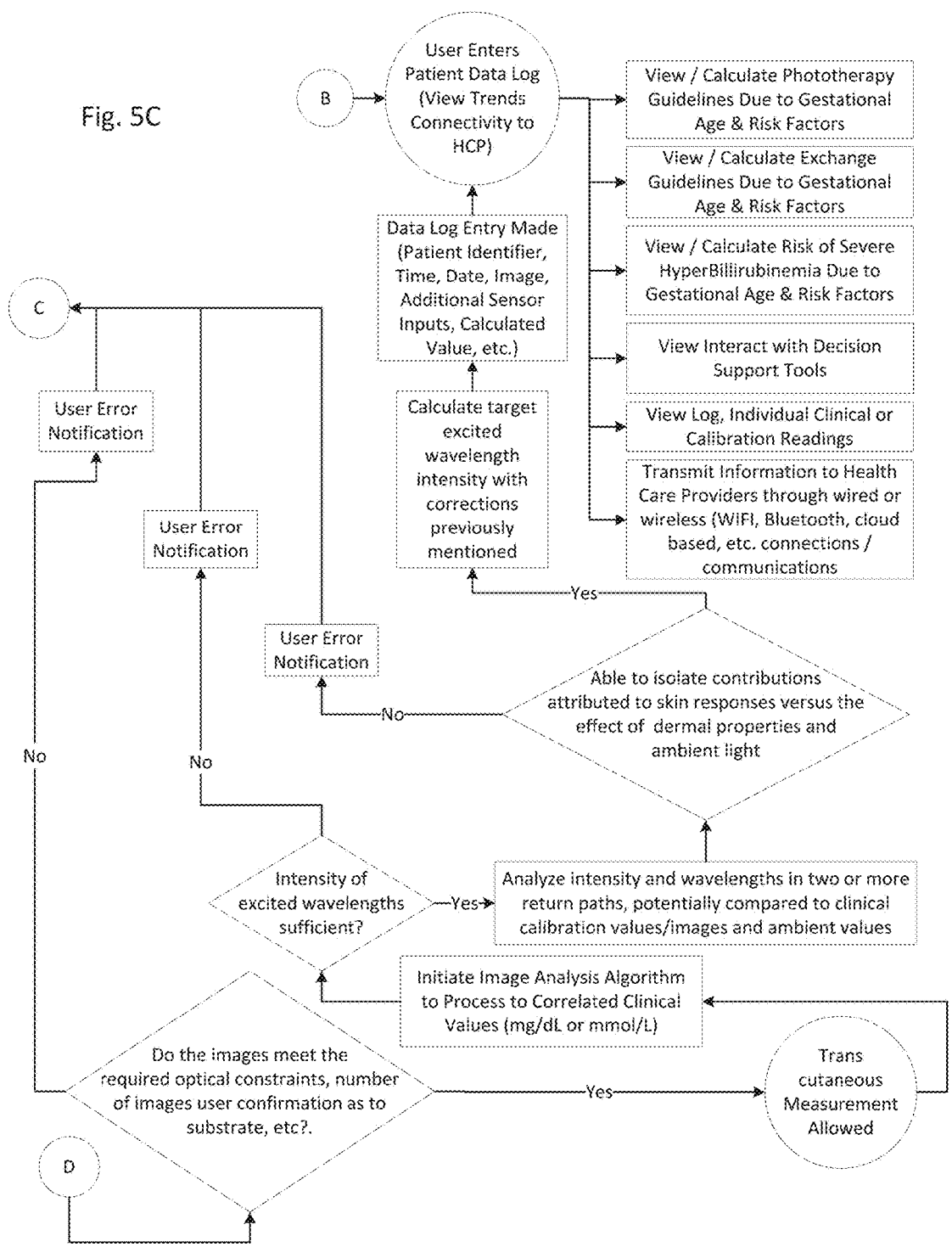
FIG. 5C is a portion of a flowchart continuing from FIGS. 5A and 5B illustrating the functions of the software of the preferred embodiment.

As seen in FIGS. 1 and 4A-4D, the invented system is based around hardware or a device 40, such as a smartphone, computer, iPod, digital camera, tablet, or other device. The device 40 provides a user interface, a light source, and an optical sensor. It also stores energy to provide power to these different components. In the preferred embodiment, the device is a smartphone such as the Nokia Lumia 1020, iPhone 5S, and the Samsung Galaxy 4, although tablets, personal computers, and other electronics will serve as well. In the preferred embodiments, the native flash of the camera is used as the source of light emission, although in other embodiments, the smartphone may control an external electronics module that emits light as well. The spectral distribution of the light source on the Nokia Lumia 1020, iPhone 5S, and the Samsung Galaxy 4 are shown in FIGS. 3A, 3B, and 3C, respectively. These Figure shows that both of the preferred 450 nm and 550 nm wavelengths are emitted by standard smartphone flashes. In preferred embodiments the camera of the smartphone is used as optical sensor, although the optical sensor may be ancillary sensors that evaluate light. Device 40 also contains a memory for storing software and data as well as a processor to execute the software. Additional sensors for detecting environmental data, such as ambient light may be included in the hardware as well.

The software 30 connects the various aspects of the invention and allows the user to interact with the controls as well as visualize the outputs of the analysis. The software controls the intensity, duration and timing sequence of the light source as well as the activation and parameters of the camera and/or sensor. It additionally can take inputs from additional sensors such as an ambient light sensor to be utilized in analysis. The software in some embodiments can analyze passive or active input from the camera to ensure the module is appropriately adhered to the hardware as well as appropriately contacting the skin substrate. The software further might prevent a calculated value to be obtained under certain constraints. In even further embodiments, it might provide visual, audible or tactile feedback to the user until the appropriate constraints are met. Once the software obtains data, it can utilize the input from the camera or sensor(s) to calculate concentrations of substances such as bilirubin within the cutaneous layer. Preferably, the software includes an algorithm that separates and analyzes the output from the return optical pathways to negate the effects of ambient light. Additionally the software could store these concentration values to provide a logged history to the user, patient, or caregivers, either directly or through wireless communications, to monitor changes and trending and to provide clinical recommendations to the patient and/or caregiver. In some embodiments, the software 30 may additionally upload and forward concentration values to a caregiver such as a doctor, nurse, or a hospital. This can be done automatically in real time or at regular intervals, or, only when requested or approved by the user possibly by way of a pop up window or side option. The software 30 may further provide reminders. For example, the software may alert a user if a reading was not been taken recently. Even further, in some embodiments, the software 30 will report device failure.

The invention also includes an ancillary module 20 as shown in FIGS. 1, 2A-2F, and 4A-4E. The ancillary module attaches to the light source and optical sensor to create a light-tight, non-transmissive barrier between these components and the patients skin. The ancillary module 20 may be attached by any known means including adhesives or interlocking parts. The light-tight feature is a vital feature of the present invention because it protects the integrity of the interface to the patient by ensuring it is appropriately in contact with the skin or other measurement substrate within acceptable pressure ranges to obtain the most accurate data. This function could be achieved through the compression of elastomeric elements 2b, 2c such as a rigid housing biased by spring loaded mechanical elements. Other possible light-tight barrier mechanisms can include inclined, ramped, or snap locking features, cases, pressure sensitive adhesives or other methods of attachment that would allow for sufficient compression of the light tight gasket(s) or seal. In some embodiments, the ancillary module further includes a mechanism for monitoring the quality of the seal. In some embodiments, the mechanism may be entirely electrical, such as a pressure sensitive touchscreen. In these embodiments, the mechanism will communicate with the software by way of the headphone jack or other input location. In other embodiments, it may be entirely mechanical. In FIG. 2, a small spring 2i loaded light sealed 2j articulating toggle 2k reacts within the appropriate pressure range to remove a shutter blocking the lightpath to the camera, as further described below, such that the software shall recognize that the ancillary module 20 is properly sealed and ready for use. The toggle 2k is hinged within the housing allowing for rotational movement. Alternatively, it may be captured within a vertical cavity of the housing and could be held in place through retention features either in the housing or the toggle. In this embodiment, prior to applying the ancillary module 20 to the skin, the tip of the retention feature would extend distally from the housing. When the user begins to place the ancillary module 20 on the patient's skin, surface tension would result in a normal force being applied on the tip of the feature, exceeding the spring force of the feature, and causing it to recoil back into the housing. The spring force of the feature could be created by a plastic molded spring arm, a compression spring, a torsional spring or through other known force, proximity, transmittance or other sensor driven actuators. The articulation of this arm would then either insert or remove a portion of the arm either into or out of a path of light returning from the skin to the camera. This aberration or lack of aberration in the light could be sensed by the phone camera and recognized as an input to the software program. A similar mechanism could also be utilized to detect the appropriate attachment of the ancillary module to the hardware, which could also be achieved through image analysis as further described in the software section below or by utilizing other sensors or actuated aberrations The ancillary module also acts as a housing to provide a light pathway 2f to enable the light source of the hardware to be directly transferred to the patient's skin. The ancillary module may contain one or more intermediate optical features such as a lens or high, low and bandpass filtering elements 2g. These options could allow light transmitted from the light source to be filtered to controlled wavelengths and transmitted with controlled losses in amplitude without interference from external sources due to the dimensional and optical characteristics of the housing components. The module could also have voids, gaps or additional light pathways or pipes 2h to allow sensors such as an ambient light sensor to have direct or indirect access to external light sources that would also influence the tissue properties and be able to be incorporated into software algorithms.

The module may further provide one or more return light pathways 2l, 2m that allow light refracted within the skin to return to the camera sensor feature. For example, the invention might include multiple parallel return light paths that capture light from two or more different dimensional pathways. These pathways may vary in size and spacing to accommodate different devices and brands. This may be accomplished by a threaded connection between the camera section and the light source section with detents set for different devices as well as additional threaded adjustment(s) to adjust the elevantion exis between the sections if desired. The several different pathways may direct light through various thicknesses of skin and allow the light to be transferred to the camera without the influence of other external sources due to the dimensional and optical characteristics of the housing components such as cavities or light pipes 2h.

The invention can be used in a multitude of embodiments, two of which are further described below. Although each embodiment is described through methods most optimal for that particular embodiment, the majority of the methods disclosed can be combined or used in parallel with other embodiments envisioned.

In the preferred embodiment the ancillary module is affixed to the device and is contacted to the skin. This is due to the fact that the alignment with the mobile device flash and camera is more critical than the alignment to the skin substrate within a jaundice patient population. The role of the interfaces could be reversed to instead adhere the ancillary module to the patient substrate or a particular target area of a substrate through a pressure sensitive adhesive patch. This would then require the hardware device to be connected to the module just during time of use, which could be accomplished through a similar light obscuring mechanism that is used on either side of the preferred embodiment or can be accomplished through other means of mechanical alignment and connection. In another embodiment, portions of the hardware utilized within the preferred embodiment could also be stored in a separate device or as part of the ancillary module to allow for additional filters or sensors not available on the hardware. The ancillary hardware could then be connected by various means of electrical connection such as through utilizing a stereo, dock or USB connection.

It will be understood by those of ordinary skill in the art that various changes may be made and equivalents may be substituted for elements without departing from the scope of the invention. In addition, many modifications may be made to adapt a particular feature or material to the teachings of the invention without departing from the scope thereof. Therefore, it is intended that the invention not be limited to the particular embodiments disclosed, but that the invention will include all embodiments falling within the scope of the claims.

The invention claimed is:

1. A system for monitoring the levels of at least one substance in skin based on the substance's optical properties, comprising:
 a device including:
  a memory;
  a processor;
  a camera coupled to said processor;
  a light source coupled to said processor; and
  a software module stored in the memory, said software module configured to run on said processor configured to control the light emitted by the light source, control the camera, and analyze at least one measurement of an amount of light from the camera to calculate concentrations of the at least one substance using an algorithm; and
 an ancillary module configured to couple to said device such that when the ancillary module is coupled to said device and placed on the skin the ancillary module creates a light-tight housing for the camera of said device,
 wherein the ancillary module comprises one or more filtering elements configured to control wavelengths of light transmitted by said light source or received by said camera, and
 wherein the ancillary module includes at least one first optical pathway configured to direct light from said light source to the skin and at least one second optical pathway configured to direct light scattered from the skin to said camera.

2. A system as claimed in claim 1 wherein the device is a mobile device.

3. A system as claimed in claim 2 wherein the mobile device is a smartphone.

4. A system as claimed in claim 2 where the mobile device is a tablet or computer.

5. A system as claimed in claim 1 wherein the ancillary module includes a sensor for measuring whether a light-tight seal has been created between said camera and the skin.

6. A system as claimed in claim 5 wherein said sensor is an electromechanical sensor.

7. A system as claimed in claim 5 wherein said sensor includes a spring-loaded element.

8. A system as claimed in claim 5 wherein said sensor is an electrical sensor.

9. A system as claimed in claim 5 wherein the said sensor is a mechanical sensor.

10. A system as claimed in claim 5 wherein said sensor includes a pressure-sensitive electrical element.

11. A system as claimed in claim 1 further comprising at least one ambient light sensor and wherein the software module is also configured to subtract a measurement of an amount of ambient light obtained from said ambient light sensor from said measurement of an amount of light measured by said camera to calculate an amount of reflected light introduced into the skin.

12. A system as claimed in claim 1 wherein the at least one substance is bilirubin.

13. A system as claimed in claim 1 wherein said at least one substance is one or more of a bodily fluid and a body product.

14. A system as claimed in claim 1 wherein said at least one substance is one or more of a drug marked for a color marker and a drug containing a color marker.

15. A system as claimed in claim 1 wherein said at least one substance is one or more of a biologic marked for a color marker and a biologic containing a color marker.

16. A system as claimed in claim 1 wherein said software module includes the native operating system of the device and an application.

17. A system as claimed in claim 1 wherein said calculation of a concentration of the at least one substance includes wavelength analysis of said at least one light measurement from said camera.

18. A system as claimed in claim 1 wherein said calculation of a concentration of the at least one substance includes a measurement of subcutaneous color of scattered light reflected by the skin.

19. A system as claimed in claim 1 wherein the said software module is configured to transmit said calculated concentration to a recipient.

20. A system as claimed in claim 19 wherein said recipient is a caregiver.

21. A system as claimed in claim 20 wherein said caregiver is one or more of a hospital, nurse, or physician.

22. A system as claimed in claim 1 wherein the said software module is configured to transmit frequency of use information to a recipient.

23. A method for determining concentration levels of at least one substance in skin based on the substance's optical properties, comprising:
   providing a device comprising:
      a processor;
      a memory coupled to said processor;
      a light source coupled to said processor;
      a camera coupled to said processor; and
      a software module stored in the memory, said software module configured to run on said processor configured to control the light emitted by the light source, control the camera, and analyze at least one measurement of an amount of light from the camera to calculate concentrations of the at least one substance using an algorithm;
   providing an ancillary module configured to couple to said device such that when the ancillary module is coupled to said device and placed on the skin the ancillary module creates a light-tight housing for the camera of said device;
   placing the said ancillary module of the device on the surface of the skin;
   activating, by said software module, the light source;
   lighting the skin using the light source;
   recording, by said camera, a measurement of scattered light from the skin; and
   calculating, by said software module, the concentration of the substance in the skin based on said measurement of scattered light from said camera,
   wherein the ancillary module comprises one or more filtering elements configured to control wavelengths of light transmitted by said light source or received by said camera, and
   wherein the ancillary module includes at least one first optical pathway configured to direct light from said light source to the skin and at least one second optical pathway configured to direct light scattered from the skin to said camera.

24. A method as claimed in claim 23 wherein the device is a mobile device.

25. A method as claimed in claim 24 wherein the said software module is configured to transmit frequency of use information to a recipient.

26. A method as claimed in claim 24 wherein the mobile device is a smartphone.

27. A method as claimed in claim 24 where the mobile device is a tablet or computer.

28. A method as claimed in claim 23 further including measuring, by a sensor of said ancillary module, whether a light-tight seal has been created between said camera and the skin.

29. A method as claimed in claim 28 wherein said sensor is an electromechanical sensor.

30. A method as claimed in claim 28 wherein the said sensor is a mechanical sensor.

31. A method as claimed in claim 28 wherein the said sensor is an electronic sensor.

32. A method as claimed in claim 28 wherein said sensor includes a spring-loaded element.

33. A method as claimed in claim 28 wherein said sensor includes a pressure-sensitive electrical element.

34. A method as claimed in claim 23 wherein the device further comprises at least one ambient light sensor and further including:
   measuring, by said ambient light sensor, an amount of ambient light obtained from said ambient light sensor;
   subtracting, by said software module, said measurement of an amount of ambient light from said measurement of an amount of light measured by said camera to calculate an amount of reflected light introduced into the skin.

35. A method as claimed in claim 23 wherein the at least one substance is bilirubin.

36. A method as claimed in claim 23 wherein said at least one substance is one or more of a bodily fluid and a body product.

37. A method as claimed in claim 23 wherein said at least one substance is one or more of a drug marked for a color marker, and drug containing a color marker.

38. A method as claimed in claim 23 wherein said at least one substance is one or more of a biologic marked for a color marker, and a biologic containing a color marker.

39. A method as claimed in claim 23 wherein said software module includes the native operating system of the device and an application.

40. A method as claimed in claim 23 wherein said calculation of a concentration of the at least one substance includes wavelength analysis of said at least one light measurement from said camera.

41. A method as claimed in claim 23 wherein said calculating of a concentration of the at least one substance includes measuring subcutaneous color of scattered light reflected by the skin.

42. A method as claimed in claim 23 wherein the said software module is configured to transmit said calculated concentration to a recipient.

43. A method as claimed in claim 42 wherein said recipient is a caregiver.

44. A method as claimed in claim 43 wherein said caregiver is one or more of a hospital, nurse, or physician.

* * * * *